(12) United States Patent
Takahashi (10) Patent No.: US 11,944,494 B2
(45) Date of Patent: Apr. 2, 2024

(54) ULTRASONIC PROBE

(71) Applicant: Hitachi, Ltd., Tokyo (JP)

(72) Inventor: Tomoo Takahashi, Tokyo (JP)

(73) Assignee: FUJIFILM HEALTHCARE CORPORATION, Kashiwa (JP)

( * ) Notice: Subject to any disclaimer, the term of this patent is extended or adjusted under 35 U.S.C. 154(b) by 391 days.

(21) Appl. No.: 16/645,079

(22) PCT Filed: Sep. 6, 2018

(86) PCT No.: PCT/JP2018/033063
§ 371 (c)(1),
(2) Date: Mar. 6, 2020

(87) PCT Pub. No.: WO2019/058987
PCT Pub. Date: Mar. 28, 2019

(65) Prior Publication Data
US 2020/0281564 A1    Sep. 10, 2020

(30) Foreign Application Priority Data
Sep. 25, 2017   (JP) .................................. 2017-183819

(51) Int. Cl.
*A61B 8/00* (2006.01)
(52) U.S. Cl.
CPC ..................... *A61B 8/4461* (2013.01)
(58) Field of Classification Search
None
See application file for complete search history.

(56) References Cited

U.S. PATENT DOCUMENTS

| | | | | | |
|---|---|---|---|---|---|
| 4,955,365 | A | * | 9/1990 | Fry | .................. G10K 11/35 601/2 |
| 5,036,855 | A | * | 8/1991 | Fry | .................. G10K 11/35 600/463 |
| 5,460,179 | A | * | 10/1995 | Okunuki | .............. A61B 8/4461 600/447 |

(Continued)

FOREIGN PATENT DOCUMENTS

| JP | S59-172371 U | 11/1984 |
|---|---|---|
| JP | 2007-267817 A | 10/2007 |

(Continued)

OTHER PUBLICATIONS

International Preliminary Report on Patentability issued in corresponding application No. PCT/JP2018/033063, dated Apr. 9, 2020, with English translation (14 pgs.).

(Continued)

*Primary Examiner* — Shahdeep Mohammed
(74) *Attorney, Agent, or Firm* — Foley & Lardner LLP (57) ABSTRACT

According to the present invention, a transducer part is mechanically scanned in a chamber for a medium. A pair of diaphragms are provided to the two sides of the transducer part (one side and the other side in the mechanical scanning direction). Each of the diaphragms has a hollow membrane and a base. The hollow membrane has a pair of longitudinal lateral surfaces extending in a longitudinal direction parallel to the center axis of rotation. An attachment hole is formed in a partition wall, and a projecting part provided on the base is inserted into the attachment hole.

9 Claims, 9 Drawing Sheets

(56) References Cited

U.S. PATENT DOCUMENTS

| | | | |
|---|---|---|---|
| 2005/0051494 A1 | 3/2005 | Na et al. | |
| 2009/0049914 A1 | 2/2009 | Hasegawa | |
| 2013/0207517 A1* | 8/2013 | Naka | H10N 30/883 310/334 |
| 2014/0236016 A1* | 8/2014 | Morgan | A61B 8/4483 600/459 |
| 2015/0051494 A1* | 2/2015 | Hwang | G10K 11/004 600/459 |
| 2018/0317883 A1* | 11/2018 | Huhtamaki | G01S 7/5208 |

FOREIGN PATENT DOCUMENTS

| | | |
|---|---|---|
| JP | 2013-165790 A | 8/2013 |
| JP | 2015-036122 A | 2/2015 |

OTHER PUBLICATIONS

International Search Report with English translation and Written Opinion issued in corresponding application No. PCT/JP2018/033063 dated Nov. 6, 2018.

* cited by examiner

ULTRASONIC PROBE

TECHNICAL FIELD

The present invention relates to an ultrasonic probe, and particularly relates to a structure of a mechanical scanning type ultrasonic probe.

BACKGROUND ART

An ultrasonic diagnostic apparatus includes an ultrasonic probe as an ultrasonic transceiver. A variety of ultrasonic probes have been put into practical use, and as one type thereof, a mechanical scanning type (mechanical scanning type) ultrasonic probe is known. The mechanical scanning type ultrasonic probe includes a transducer unit (transducer assembly) as a movable body and a scan mechanism (scan system) that mechanically scans the transducer unit. The transducer unit includes a single transducer unit or a transducer array. For example, a three-dimensional echo data acquisition space is formed by mechanically moving the transducer unit including a one-dimensional transducer array. Such an ultrasonic probe is also referred to as a mechanical scanning type 3D probe. As the mechanical scanning type ultrasonic probe, a probe that comes into contact with a surface of a body and a probe that is inserted into a body cavity are known.

The mechanical scanning type ultrasonic probe has a medium chamber forming a motion space of the transducer unit. The medium chamber is filled with an acoustic propagation medium as a liquid. With such a configuration, an air layer is eliminated from an ultrasonic propagation path between the transducer unit and a film body (a cap defining the medium chamber), and good acoustic propagation is ensured. A volume of the acoustic propagation medium changes due to changes in temperature and the like. In order to absorb the change and balance pressure in the medium chamber with atmospheric pressure, a diaphragm (diaphragm device) (pressure regulator) is provided in the mechanical scanning type ultrasonic probe.

An ultrasonic probe disclosed in PTL 1 has a diaphragm provided outside a medium chamber. An inside of the diaphragm communicates with an inside of the medium chamber, and an acoustic propagation medium is accommodated in the diaphragm.

An ultrasonic probe disclosed in PTL 2 has a diaphragm including two deformation portions. The two deformation portions include a deformation portion protruding to an outside of a medium chamber and a deformation portion protruding toward an inside of the medium chamber. Two wires pass through centers of the deformation portions, and the two deformation portions follow the movement of the two wires so as to perform follow-up deformation in opposite directions with each other, thereby maintaining the volume of a space in which a medium is accommodated.

PRIOR ART LITERATURE

Patent Literature

PTL 1: JP-A-2007-267817
PTL 2: JP-A-2015-036122

SUMMARY OF INVENTION

Technical Problem

In the mechanical scanning type ultrasonic probe, the medium chamber is provided in a case, and the transducer unit moves in the medium chamber. Typically, the transducer unit rotates (swings) around a rotation central axis orthogonal to a probe central axis. In such a configuration, a useless space (dead space) is likely to be generated at both sides of the transducer unit (one side and another side in a mechanical scanning direction) and close to a partition wall. In order to reduce an amount of the acoustic propagation medium filled into the media chamber, it is desirable to reduce the useless space.

As disclosed in PTL 1, when the diaphragm is provided outside the medium chamber, it is necessary to ensure a space for the diaphragm, and in some cases, problems occur in that a size of the probe increases or a form of the probe is restricted. The diaphragm disclosed in PTL 2 is deformed by moving the two wires, and is different from the original diaphragm deformed by the pressure difference.

An object of the invention is to reduce the amount of an acoustic propagation medium in a medium chamber in a mechanical scanning type ultrasonic probe. Alternatively, a dead space in the medium chamber is utilized. Another object of the present invention is to realize a structure capable of installing the diaphragm without ensuring a space for installing the diaphragm outside the medium chamber.

Solution to Problem

An ultrasonic probe according to the invention includes: a case; a partition wall that is disposed in the case; a scanning mechanism configured to mechanically scan a transducer unit transmitting and receiving ultrasonic waves, in a medium chamber that is formed between the case and an inner surface of the partition wall; and a pair of diaphragms that is provided on both sides of the transducer unit in a mechanical scanning direction in the medium chamber, that has a form protruding from the inner surface of the partition wall to a living body side, and that adjusts internal pressure of the medium chamber.

DESCRIPTION OF EMBODIMENTS (1) Overview of Embodiment

An ultrasonic probe according to an embodiment includes a case, a partition wall, a transducer unit, a scanning mechanism, and a pair of diaphragms. The partition wall is provided in the case, and a medium chamber is formed between the case and an inner surface of the partition wall. The scanning mechanism mechanically scans the transducer unit in the medium chamber. The pair of diaphragms in the medium chamber is provided on both sides of the transducer unit in a mechanical scanning direction, has a form protruding from the inner surface of the partition wall to a living body side, and adjusts internal pressure of the medium chamber.

An empty space is likely to be generated on both sides (one side and another side in the mechanical scanning direction) of the transducer unit in the medium chamber. The above-described configuration effectively utilizes the empty space, and the pair of diaphragms is disposed therein. Since the volume of the pair of diaphragms and the volume of the medium chamber are reduced, an amount of an acoustic propagation medium to be filled into the medium chamber is reduced. As a result, weight of the ultrasonic probe is reduced. In a case where the diaphragms are provided outside the medium chamber, problems may occur in that a size of the probe increases or a form of the probe is restricted, but according to the above-described configuration, such problems do not occur. Since the diaphragms are provided on one side and the other side of the transducer unit respectively, weight balance is improved.

In the embodiment, an atmospheric pressure chamber is formed between the case and an outer surface of the partition wall, and an inside of each of the diaphragms communicates with the atmospheric pressure chamber. According to this configuration, it is possible to naturally balance the internal pressure of the medium chamber with atmospheric pressure.

In the embodiment, the scanning mechanism swings the transducer unit around a rotation central axis orthogonal to a probe central axis, and each of the diaphragms is a hollow member having a pair of longitudinal side surfaces extending in a longitudinal direction parallel to the rotation central axis and a pair of lateral side surfaces provided between the two longitudinal side surfaces.

In a case where it is assumed that the partition wall is formed in a substantially flat plate shape, if the transducer unit swings around the rotation central axis, a relatively large empty space having a form extending in a direction parallel to the rotation central axis is likely to be generated at one side and another side of the transducer unit in the mechanical scanning direction close to the partition wall. The above-described configuration effectively utilizes the empty space to dispose the pair of diaphragms having the form extending in the direction parallel to the rotation central axis. According to the above configuration, when the diaphragm is deformed, deformation of each of the longitudinal side surfaces becomes dominant, and thus, an increase in the height (length) of each of the diaphragms can be suppressed. Thus, even if an initial protrusion amount (a protrusion amount in an original state) of each of the diaphragms is relatively large, contact between each diaphragm and the transducer unit is avoided.

According to the embodiment, an end portion of the living body side in each of the diaphragms has a rounded dome shape when viewing from the longitudinal direction. According to such a configuration, a turbulence flow generated and caused by the individual diaphragms can be reduced. When a cable or the like is disposed in the medium chamber, the cable is hardly caught by the diaphragm.

In the embodiment, even when the transducer unit that performs mechanically scanning is the closest to the pair of diaphragms, the pair of the diaphragms is provided on both sides of the transducer unit in the mechanical scanning direction, so that a condition that the pair of the diaphragms does not come into contact with the transducer unit is satisfied.

In the embodiment, each of the diaphragms includes a pedestal attached to the partition wall and a hollow film that is attached to the pedestal and is elastically deformed, and a vent passage that communicates the inside of the diaphragm with a space outside the partition wall is formed for each of the diaphragms. According to this configuration, it is easy to attach the diaphragm to the partition wall and to form the vent passage.

In the embodiment, an attachment structure is provided across the diaphragm and the partition wall for each of the diaphragms. Each attachment structure includes a protruding portion formed on one of the pedestal and the partition wall, and a hole portion formed on the other of the pedestal and the partition portion and into which the protruding portion is inserted, and the vent passage is formed so as to penetrate the attachment structure. According to this configuration, when the diaphragms are disposed, positioning is facilitated, and the vent passage can be reliably ensured.

In the embodiment, the protruding portion is formed on the pedestal, a through hole is formed along a central axis of the protruding portion, and the hole portion is an attaching hole which is formed in the partition wall and into which the protruding portion is inserted. According to the embodiment, in each of the diaphragms, the hollow film has an attachment end portion that covers a side peripheral surface of the pedestal, and each of the diaphragms has a band that suppresses the attachment end portion from an outside of the attachment end portion to the side peripheral surface of the pedestal. If the attachment end portion is sandwiched between the pedestal and the band, even if an increase or decrease of the pressure is repeated, a sealing state can be reliably maintained.

(2) Details of Embodiment

Figure 1:
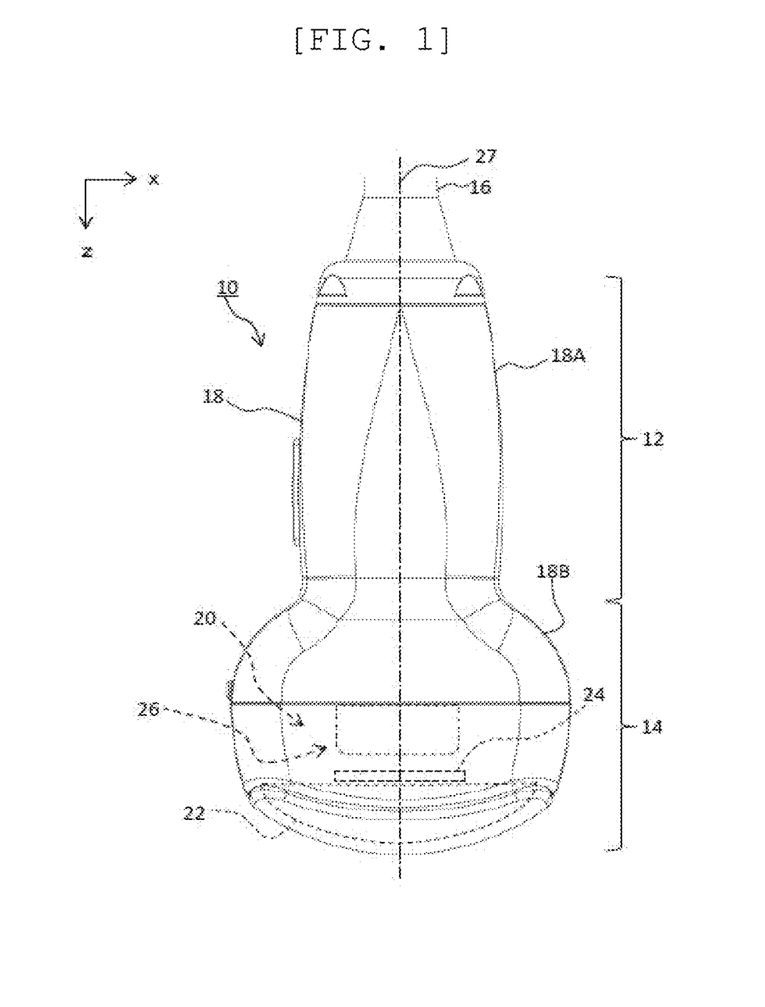
FIG. 1 is a front view of an ultrasonic probe according to an embodiment.

FIG. 1 illustrates the ultrasonic probe according to the embodiment. An ultrasonic probe 10 is used in ultrasonic diagnosis of a living body, and is used, for example, in an abdominal examination in the living body. The ultrasonic probe 10 is a mechanical scanning type 3D probe. The ultrasonic probe 10 is connected to an ultrasonic diagnostic apparatus main body (not shown).

The ultrasonic diagnostic apparatus is configured by the ultrasonic diagnostic apparatus main body and the ultrasonic probe. The ultrasonic diagnostic apparatus main body includes a transmission circuit that supplies a transmission signal to the ultrasonic probe, a reception circuit that processes a reception signal from the ultrasonic probe, and an image forming circuit that forms an ultrasonic image based on the signal output from the reception circuit. Examples of the ultrasonic image include a tomographic image representing a biological cross-section, a blood flow image representing blood flow in the living body, and a rendering image representing a three-dimensional space in the living body.

The ultrasonic probe 10 includes a grip portion 12 and a tip end portion 14. The grip portion 12 is a part on a non-living body side, and the tip end portion 14 is a part on a living body side. In a configuration example illustrated in the drawing, the tip end portion 14 is larger than the grip portion 12. Typically, a grip portion is held by a user. Of course, the tip end portion 14 may be held by the user.

The ultrasonic probe 10 has a hollow case 18 made of resin or the like. The case 18 is roughly divided into an upper case 18A in the grip portion 12 and a lower case 18B in the tip end portion 14. A probe cable 16 is pulled out from an upper end of the upper case 18A. It is also possible to configure the ultrasonic probe 10 as a wireless probe. A pressure adjustment technique described below may be applied to a body cavity insertion type ultrasonic probe. For example, an embedded pressure regulator to be described later may be provided in a head of a transvaginal probe or a transrectal probe.

The partition wall, which will be illustrated later, is provided in the case 18. The partition wall is a substantially flat plate-shaped structure extending in a direction orthogonal to a probe central axis 27. In the case 18, a medium chamber 20 is defined on the living body side of the partition wall. The medium chamber 20 is a sealed space and is filled with the acoustic propagation medium such as insulating oil. A transducer unit 22 performs mechanically scanning in the medium chamber 20. A shaft member 24 is provided in parallel to the direction orthogonal to the probe central axis. A central axis of the shaft member 24 is the rotation central axis. The transducer unit 22 rotates (swings) around the rotation central axis. In FIG. 1, a z direction is a direction parallel to the probe central axis, and an x direction is a direction orthogonal to the z direction and parallel to the rotation central axis. A y direction is orthogonal to the x direction and the z direction.

In the ultrasonic probe according to the embodiment, an embedded pressure regulator 26 is provided in the medium chamber 20. Specifically, as the embedded pressure regulator 26, the pair of the diaphragms are provided on both sides (the one side and the other side in the mechanical scanning direction (y direction)) of the transducer unit 22. Each diaphragm performs a pressure adjustment function independently. That is, due to self-deformation (shrunk deformation or expansion deformation), an equilibrium state is formed between the pressure in the medium chamber 20 and the atmospheric pressure. Accordingly, sealing property in the medium chamber 20 is maintained. That is, occurrence of leakage caused by atmospheric pressure variation, volume variation due to temperature change of the acoustic propagation medium, and the like is prevented. In addition, if the pair of the diaphragms is provided in the medium chamber 20, a filling amount of the acoustic propagation medium can be reduced by that amount, so that advantages such as weight reduction and easy maintenance are obtained. For example, when the pressure regulator is disposed in the upper case 18A, there are problems that the size of the upper case 18A must be increased and restriction on a structure of the upper case 18A is caused (particularly, a problem that leads to a decrease in operability). In contrast, according to the configuration of the embodiment, such problems do not occur.

Figure 2:
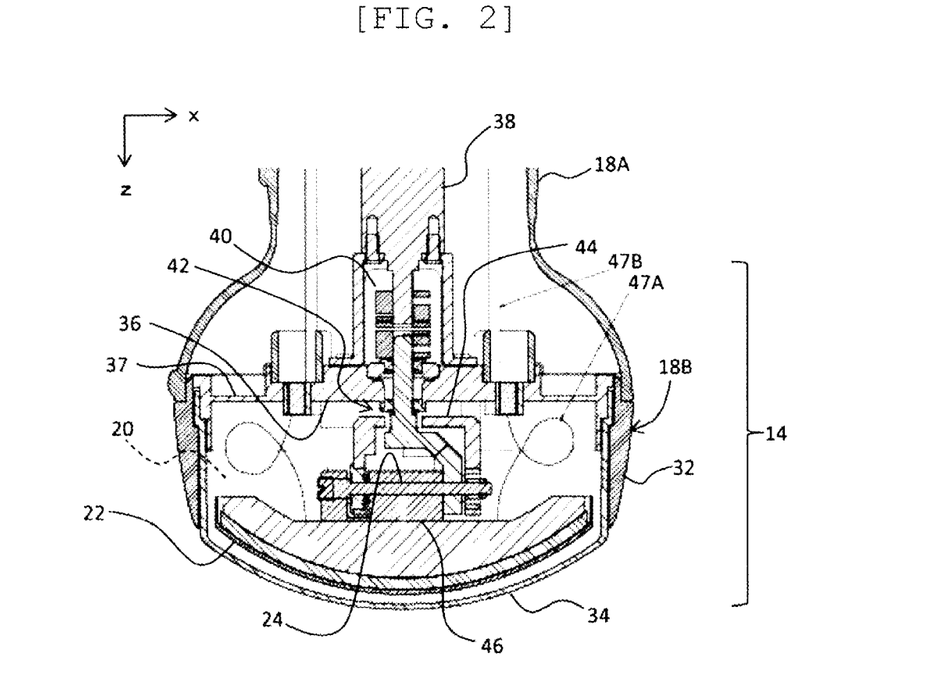
FIG. 2 is a cross-sectional view illustrating an xz cross section of the ultrasonic probe illustrated in FIG. 1.

FIG. 2 illustrates an xz cross section (particularly, an xz cross section of the tip end portion 14) of the ultrasonic probe. FIG. 2 does not show the embedded pressure regulator illustrated in FIG. 1. It is to be noted that schematic hatching is applied to each cross-sectional view in the application.

In the illustrated configuration example, the lower case 18B includes an annular holder 32 and a hollow film body 34 held by the annular holder. The film body 34 has a cap-shaped structure and is made of a resin or the like having an acoustic impedance close to the acoustic impedance of the living body. An outer surface of the film body 34 (lower surface in FIG. 2) is brought into contact with a surface of the living body.

In the lower case 18B, a generally flat plate shaped partition wall 36 extending in the direction orthogonal to the probe central axis is provided. The partition wall 36 vertically divides an inside of the lower case 18B. The partition wall 36 functions as housing or a base and is made of a metal, such as aluminum. From a viewpoint of reducing the weight of the ultrasonic probe, several positions of the partition wall 36 are formed as thin portions 37.

The medium chamber 20 is formed on the living body side of the partition wall 36, and the transducer unit 22 is provided to be movable in the medium chamber 20. The transducer unit 22 has a one-dimensional transducer array including a plurality of transducer elements arranged in a circular arc shape. An ultrasonic beam is formed by the transducer array, and scanning is electronically performed with the ultrasonic beam. In the present embodiment, an electronic convex scanning method is adopted as one type of electronic linear scanning methods. Other electronic scanning methods may be adopted. For example, an electronic sector scanning method may be adopted. In the embodiment, scanning in a fan shape is electronically performed with the ultrasonic beam. While such electron scanning is repeatedly performed, the transducer unit 22 performs reciprocating scanning mechanically. As a result, a three-dimensional echo data acquisition space is repeatedly formed.

In the transducer unit 22, a matching layer is provided on the living body side of the transducer array, and an acoustic lens is provided on the living body side of the matching layer. A surface of the acoustic lens faces an inner surface of the film body 34 with a small gap therebetween. A backing that absorbs or attenuates ultrasonic waves is provided on the non-living body side of the transducer array, and the backing is attached to a hard movable base.

In the upper case 18A, a motor 38 served as a driving source is disposed in the illustrated configuration example. A drive shaft of the motor 38 is connected to a scanning mechanism 42 via a coupling 40. The scanning mechanism 42 swings the transducer unit 22 around the rotation central axis. The scanning mechanism 42 includes a shaft, a driving-side bevel gear, a driven-side bevel gear, the shaft member 24, and the like. The central axis of the shaft member 24 is the rotation central axis. The rotation central axis is parallel to the x direction. A frame 44 rotatably holds the shaft member 24 while accommodating the driving-side bevel gear, the driven-side bevel gear, and the like. The frame 44 is fixed to the partition wall 36. The frame 44 includes a bifurcated portion opened to the living body side, and the bifurcated portion rotatably holds two portions on the shaft member 24. A connecting member 46 made of a metal block is provided to connect the frame 44 and the transducer unit 22. The connecting member 46 is fixed to the shaft member 24.

The transducer unit 22 is a movable body, and a plurality of cables (for example, a plurality of FPC sheets) are drawn therefrom. The cables are drawn out from the medium chamber 20 to a space in which the motor 38 is accommodated (see reference numerals 47A and 47B). A tip end portion of the motor 38 is held by a holding member, and the holding member is fixed to the partition wall 36. The motor 38 is fixed in a cantilever manner.

The frame 44 accommodating a part of the scanning mechanism 42 is provided at a central portion in the x direction and a central portion in the y direction of the medium chamber 20. A plurality of the cables are drawn out by using spaces on a right side and a left side in the x direction in the medium chamber 20. As a result, in the medium chamber 20, empty spaces are generated on both sides of the frame 44 in the y direction (on both sides in the mechanical scanning direction of the transducer unit 22 and close to the partition wall 36). The empty spaces are used as spaces for arranging the pair of the diaphragms.

Figure 3:
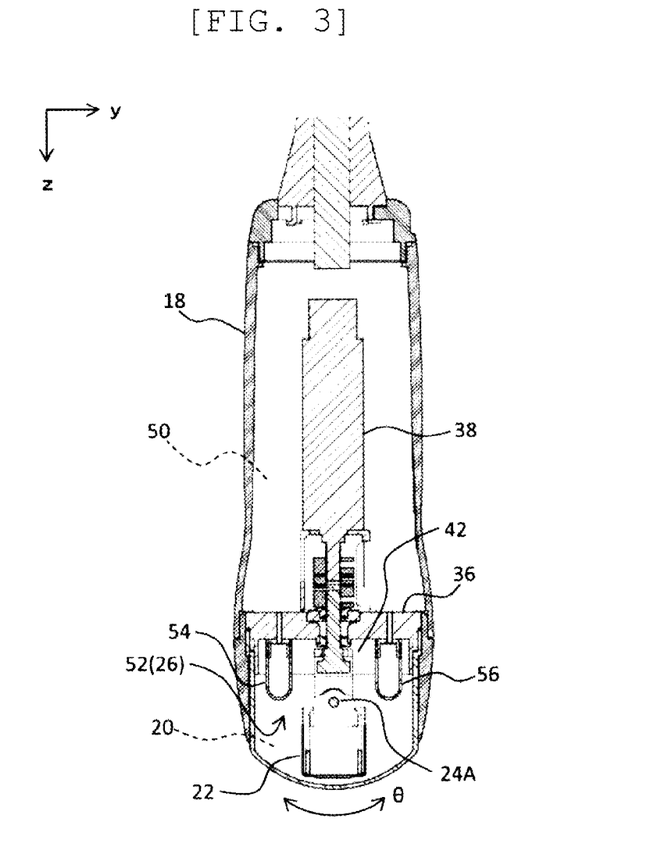
FIG. 3 is a cross-sectional view illustrating a yz cross section of the ultrasonic probe illustrated in FIG. 1.

FIG. 3 illustrates a yz cross section of the ultrasonic probe. An inside of the case 18 is divided by the partition wall 36, the medium chamber 20 is defined on the living body side of the partition wall 36, and a motor accommodation chamber 50 is defined on the non-living body side of the partition wall 36. The motor accommodation chamber 50 is also referred to as an atmospheric pressure chamber. The motor 38 is disposed in the motor accommodation chamber 50. The transducer unit 22 and the scanning mechanism 42 are provided in the medium chamber 20. Reference numeral 24A illustrates an end of the shaft member. An arc-shaped mechanical scanning direction is represented by θ. The arc-shaped mechanical scanning direction is orthogonal to an arc-shaped electronic scanning direction.

In the medium chamber 20, a pair of diaphragms 54, 56 is provided as the embedded pressure regulator 26. Specifically, a pair of diaphragms 52 is provided on both sides of the transducer unit 22 in the θ direction and close to the partition wall 36. Specifically, each of the diaphragms 54, 56 is fixed to the partition wall 36, and has a form in which the diaphragms 54, 56 protrude from an inner surface thereof to the living body side. When the transducer unit 22 swings, the form, a position disposition, and the like of each of the diaphragms 54, 56 are determined, so as to satisfy a condition in which the diaphragms 54, 56 are not in contact with the transducer unit 22. An internal space of each of the diaphragms 54, 56 communicates with the motor accommodation chamber 50. That is, pressure in the internal space of each of the diaphragms 54, 56 is maintained at the atmospheric pressure.

Figure 4:
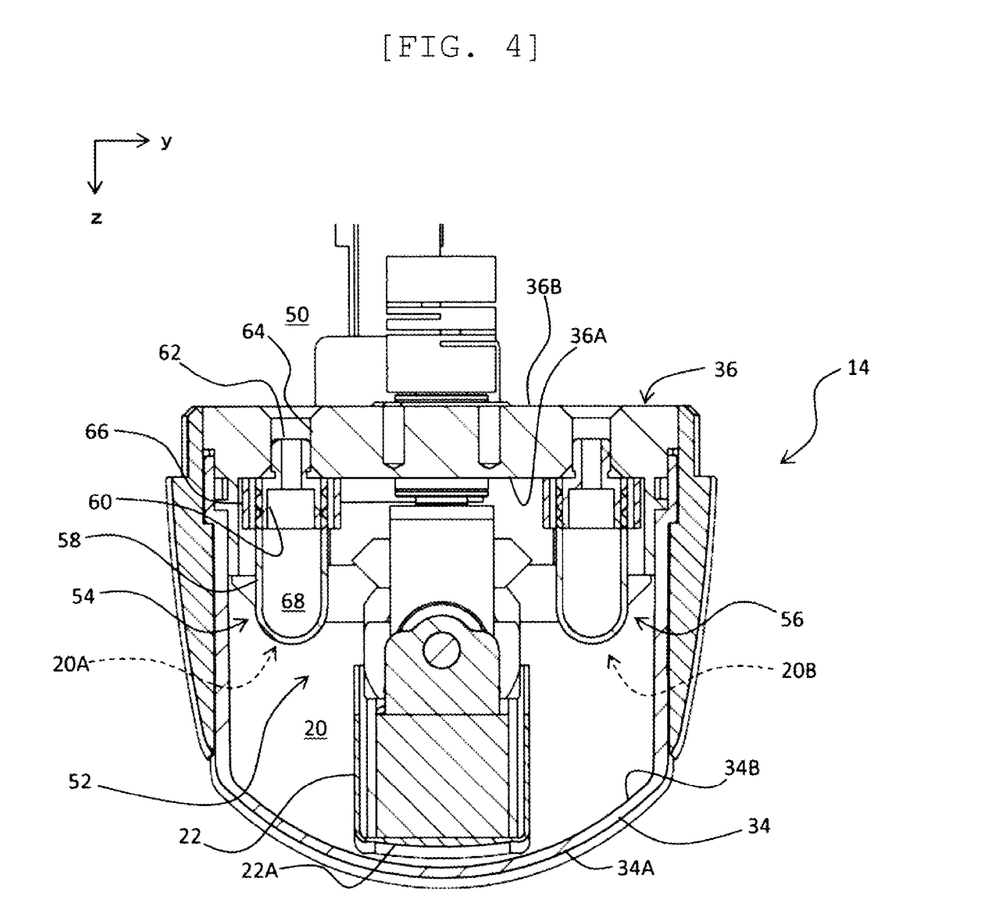
FIG. 4 is an enlarged cross-sectional view of a tip end portion.

FIG. 4 illustrates an enlarged cross section of the tip end portion 14. The partition wall 36 has an inner surface 36A and an outer surface 36B. The inner surface 36A is a surface facing the living body side, and the outer surface 36A is a surface facing the non-living body side. A space surrounded by the inner surface 36A and the film body 34 is the medium chamber 20. The motor accommodation chamber 50 is formed on the outer surface 36B. The film body 34 includes an outer surface 34A and an inner surface 34B. The outer surface 34A is in contact with the surface of the living body. The transducer unit 22 has a wave transmitting/receiving surface 22A as the surface of the acoustic lens, and the wave transmitting/receiving surface 22A faces the inner surface 34B via a gap. Even when the transducer unit 22 swings, a non-contact state between the wave transmitting/receiving surface 22A and the inner surface 34B is maintained.

The pair of the diaphragms 52 includes the diaphragm 54 and the diaphragm 56. They are in the medium chamber 20 and are disposed in a pair of partial spaces 20A, 20B and close to the partition wall 36 and both sides of the transducer unit 22. As described above, in general, the partial spaces 20A, 20B are empty spaces (dead spaces). In order to utilize the partial spaces, the pair of the diaphragms 54, 56 is disposed therein. In the embodiment, the diaphragms 54, 56 have the same configuration. Therefore, in the following description, a specific configuration will be described as a representative of the diaphragm 54. However, depending on disposition conditions and the like, the forms and the like may be different between the diaphragms 54, 56.

The diaphragm 54 includes a hollow film 58 and a pedestal 60. The pedestal 60 has an elongated shape extending in the x direction (the direction parallel to the rotation central axis) and is made of a metal such as aluminum. The pedestal 60 includes a cylindrical-shaped protruding portion 62 protruding toward the non-living body side. The through hole that forms the vent passage is formed along a central axis of the protruding portion 62. Meanwhile, a circular attaching hole 64 corresponding to the diaphragm 54 is formed in the partition wall 36. Another attaching hole corresponding to the diaphragm 56 is also formed in the partition wall 36. In a state in which the protruding portion 62 is inserted or fitted into the attaching hole 64, the pedestal 60 is fixed to the partition wall 36 by an adhesive. In this case, means such as screwing may be used.

The attaching hole 64 and the protruding portion 62 form the attachment structure. The attaching hole may be formed on a side of the pedestal 60, and the protruding portion may be formed downward on a side of the partition wall 36. A plurality of protruding portions may be formed in the diaphragm 54, and a plurality of attaching holes corresponding to the protruding portions may be formed in the partition wall 36. According to the attachment structure, advantages such as easy in positioning and assembling can be obtained. The attachment structure exerts functions of optimizing positions and postures of the diaphragms 54, 56 and preventing a contact between the diaphragms 54, 56 and the transducer unit 22.

The hollow film 58 is made of an elastically deformable rubber material. The thickness of the hollow film 58 is, for example, 0.5 mm. The hollow film 58 has a form extending in the x direction. In the hollow film 58, the x direction is the longitudinal direction, and the y direction is a lateral direction. The z direction is a protruding direction (height direction). As shown later, four side surfaces of the hollow film 58 include two longitudinal side surfaces and two lateral side surfaces. The attachment end portion (upper end portion in FIG. 4) of the hollow film 58 covers a side peripheral surface of the pedestal 60 and the attachment end portion and the side peripheral surface are in contact with each other. Further, the attachment end portion thereof and a band 66 are in contact with each other while the attachment end portion thereof is covered by the band 66. The band 66 is formed of an elastic member and applies a holding force for pressing the attachment end portion toward a side peripheral surface side of the pedestal 60. A tip end portion (lower end portion in FIG. 4) of the hollow film 58 has a rounded dome shape when viewed from the x direction (that is, the longitudinal direction). An internal space 68 of the diaphragm 54 communicates with the motor accommodation chamber 50. A space between the internal space 68 of the diaphragm 54 and the medium chamber 20 is completely sealed. That is, the acoustic propagation medium does not leak to an outside through the diaphragm 54, and air does not enter the medium chamber 20.

Figure 5:
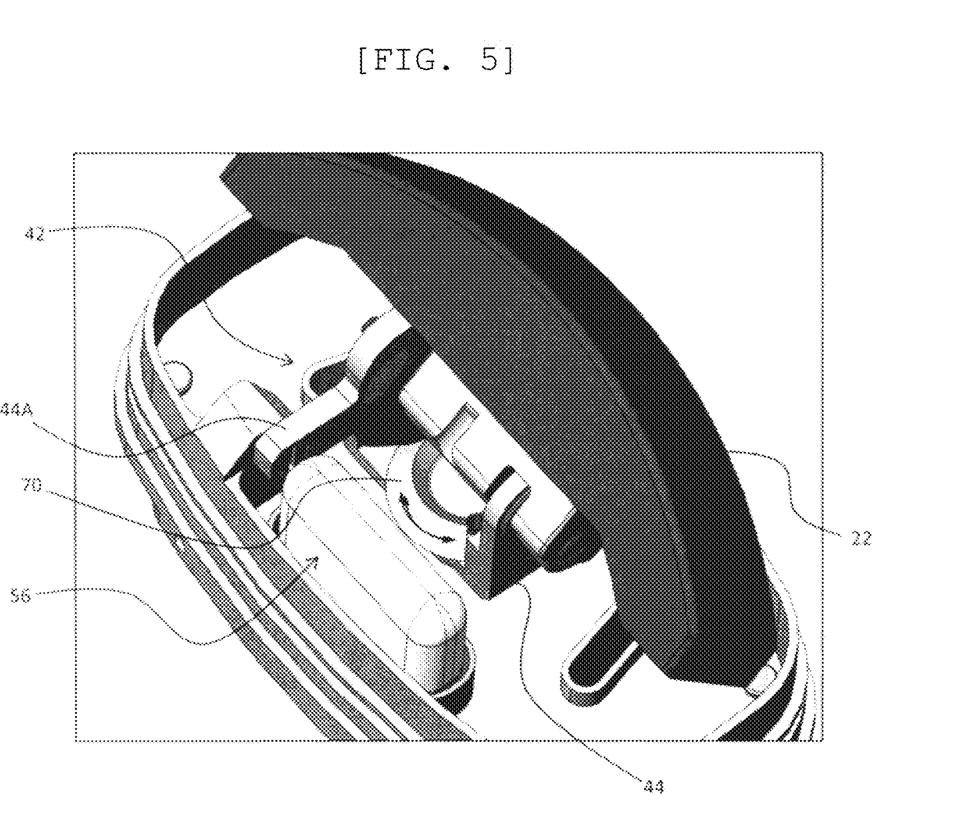
FIG. 5 is a perspective view illustrating one of diaphragms.

FIG. 5 is a perspective view of the tip end portion. The lower case is erased on the drawing. The transducer unit 22 has a tilted posture by the effect of the scanning mechanism 42. In FIG. 5, a bevel gear 70 on a driving-side included in the scanning mechanism 42 appears. The bevel gear 70 reciprocates in a positive direction and a negative direction. An arm portion 44A is configured as a part of the frame 44 and is fixed to the partition wall. The diaphragm 56 is provided with a positional relationship that does not collide with these members. The other diaphragm on the opposite side does not appear in FIG. 5. As shown in the drawing, the diaphragm 56 has the form extending in the direction parallel to the rotation central axis. In other words, the diaphragm 56 is formed with two longitudinal side surfaces extending in the longitudinal direction. Each of the two longitudinal side surfaces functions as a deformation surface.

Figure 6:
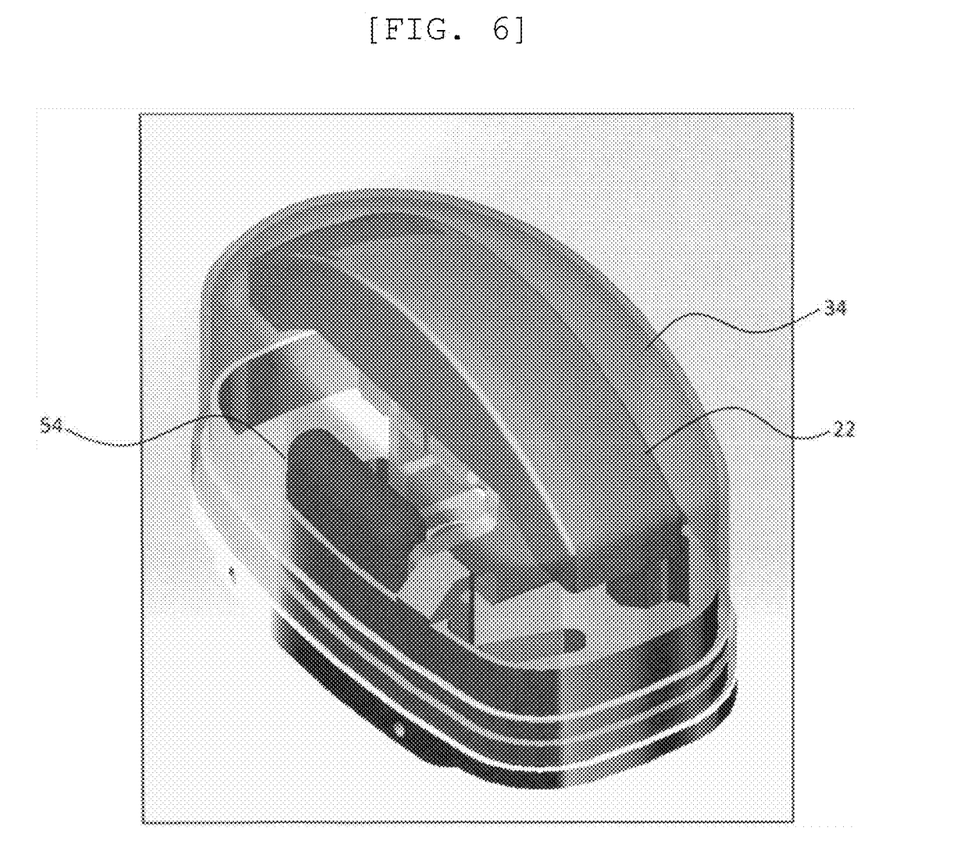
FIG. 6 is a transparent view illustrating the other of the diaphragms.

FIG. 6 is a transparent view of the tip end portion. The film body 34 is represented by a transparent member. The transducer unit 22 in a standing posture appears in the film body 34. The diaphragm 54 is provided on one side of the transducer unit 22. Similar to the diaphragm on the other side, the diaphragm 54 has the form extending in the direction parallel to the rotation central axis. In other words, the diaphragm 54 is formed with two longitudinal side surfaces extending in the longitudinal direction. Each of the two longitudinal side surfaces functions as a deformation surface in the similar manner as described above.

Figure 7:
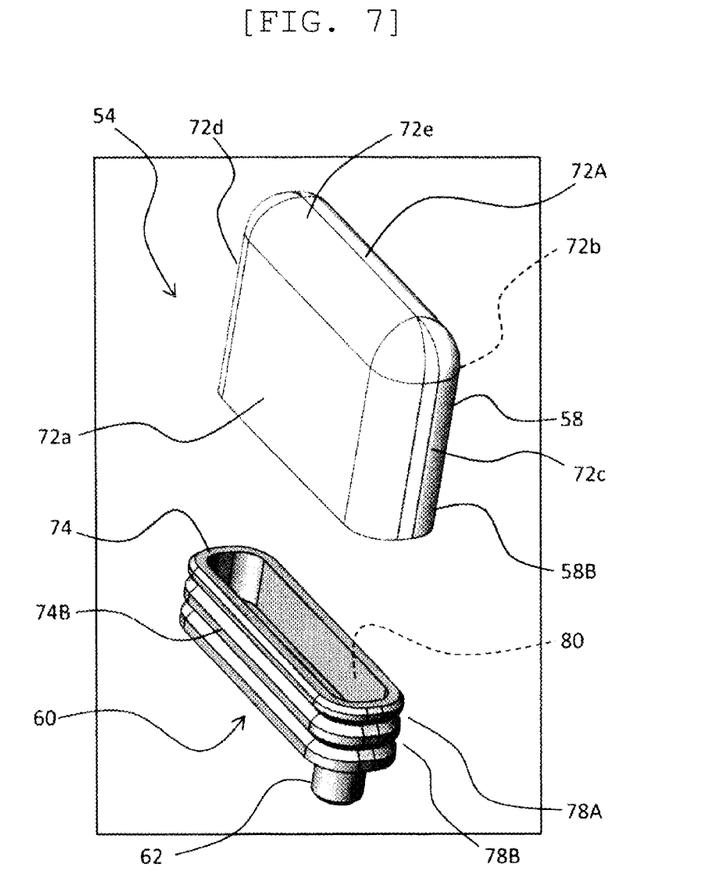
FIG. 7 is an exploded perspective view of the diaphragm.

FIG. 7 is an exploded perspective view of the diaphragm 54. As described above, the diaphragm 54 includes the hollow film 58 and the pedestal 60. The pedestal 60 includes a pedestal body 74 and the protruding portion 62. The protruding portion 62 protrudes from the pedestal body 74 toward the non-living body side, and has a form in a cylindrical shape. The pedestal body 74 has a form extending in the longitudinal direction (direction parallel to the rotation central axis), and specifically has a rectangular form having four rounded corner portions when viewed from the living body side, or has a form close to a long ellipse. In order to avoid other structures provided on the partition wall, the protruding portion 62 is provided at a position shifted to one side in the longitudinal direction of the pedestal body 74. If such avoidance is not necessary, the protruding portion 62 may be provided at a central position in the longitudinal direction. The pedestal body 74 is formed of a bottom wall and a peripheral wall, and an internal space 80 thereof has a groove shape.

As described above, the hollow film 58 has the longitudinal direction and the lateral direction, and specifically has two longitudinal side surfaces 72a, 72b and two lateral side surfaces 72c, 72d. The two longitudinal sides 72a, 72b are in a parallel relationship. The two longitudinal sides 72a, 72b and the two lateral sides 72c, 72d are in a generally orthogonal relationship. However, when viewed from the protruding direction (z direction) of the hollow film 58, the two lateral side surfaces 72c, 72d bulge outward, that is, have rounded forms. The two lateral side surfaces 72c, 72d are smoothly connected to the two longitudinal side surfaces 72a, 72b. The two longitudinal side surfaces 72a, 72b and the two lateral side surfaces 72c, 72d are connected to a tip end surface 72e to be described below. The hollow film 58 is a thin film. When the thickness is substantially ignored, individual surfaces correspond to individual walls or film portions. A width of the diaphragm 54 in the longitudinal direction is, for example, twice or more the width of the diaphragm 54 in the lateral direction, and is preferably 2.5 times or more.

A tip end portion (a portion corresponding to the tip end surface 72e) 72A on the living side of the hollow film 58 has a rounded dome shape when viewed from the longitudinal direction. When viewed from the lateral direction, both ends of the tip end portion 72A are rounded. When an attachment end portion 58B on the non-living side of the hollow film 58 covers a side peripheral surface 74B of the pedestal body 74, and is attached thereto. For such an attachment, an adhesive is used. In order to improve adhesion or a degree of coupling between the side peripheral surface 74B and the attachment end portion 58B, two annular grooves 78A, 78B are formed on the side peripheral surface 74B. The annular grooves 78A, 78B function as spaces for storing the adhesive, and function to cause unevenness on the side peripheral surface 74B so as to increase the degree of coupling with the attachment end portion 58B. One annular groove or three or more annular grooves may be provided. Other structures may be adopted to enhance the adhesion. In FIG. 7, the bands are not shown.

Figure 8:
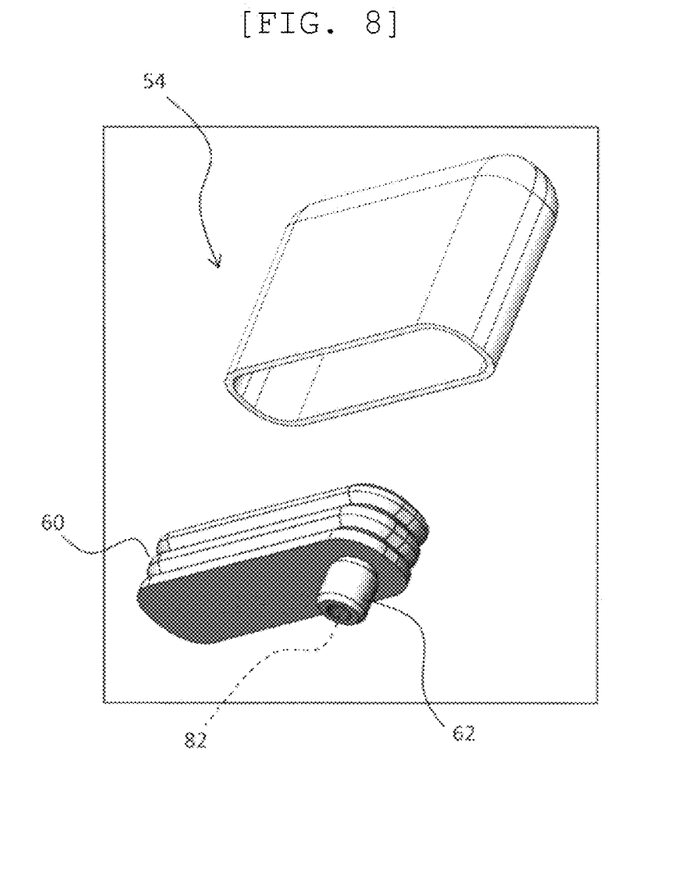
FIG. 8 is another exploded perspective view of the diaphragm.

FIG. 8 is another exploded perspective view of the diaphragm 54. A through hole 82 functioning as a vent hole is formed in the protruding portion 62 provided on the pedestal 60.

Figure 9:
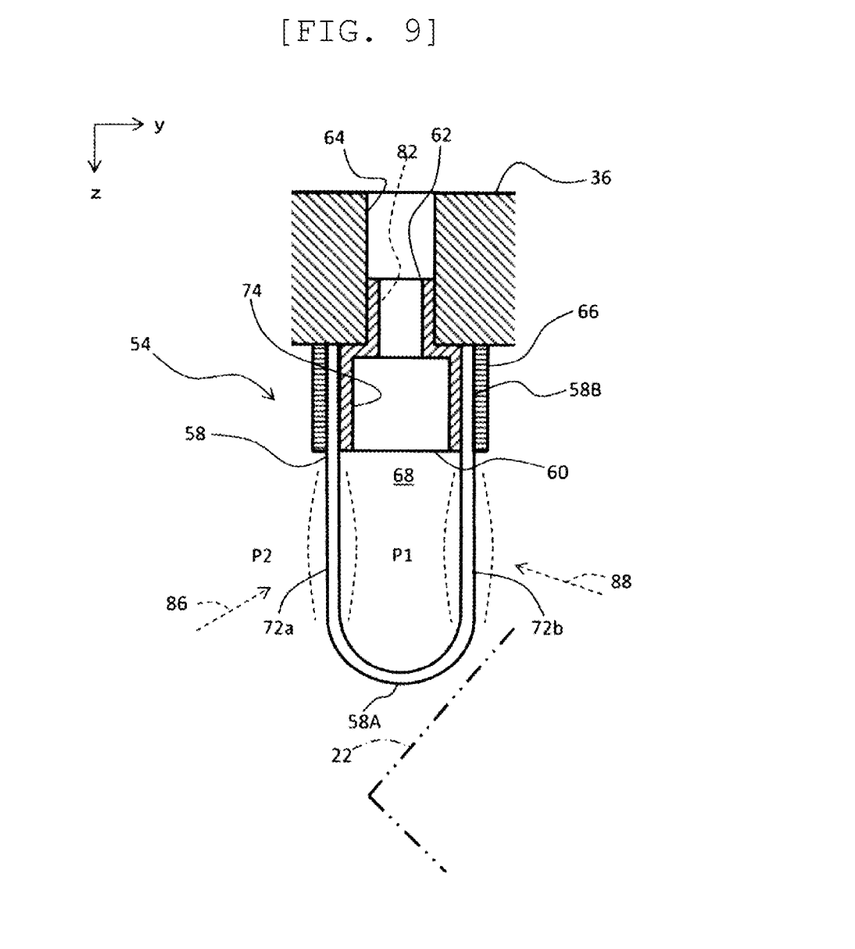
FIG. 9 is a cross-sectional view of the diaphragm.

FIG. 9 illustrates a yz cross section of the diaphragm 54. The attachment end portion 58B of the hollow film 58 covers the side peripheral surface of the pedestal body 74 of the pedestal 60, and the outside of the attachment end portion 58B is covered by the band 66. A plurality of laminated members are firmly bonded to each other by the adhesive. Even when the band 66 is not provided, peeling of the attachment end portion can be prevented, but the peeling can be more reliably prevented when using the band 66.

The protruding portion 62 of the pedestal 60 is inserted into the attaching hole 64 formed in the partition wall 36, and in the inserted state, the pedestal 60 is fixed to the partition wall 36 by the adhesive. The advantage of easy in positioning during assembly can be obtained by using the attachment structure. That is, it is possible to reliably prevent the contact between the diaphragm 54 and the transducer unit by arranging the diaphragm 54 in a correct position and in a correct posture.

When pressure in the internal space 68 of the diaphragm 54 is set as P1 and pressure in the medium chamber is set as P2, and if the P2 is higher than the P1, the hollow film 58 is shrunk and deformed. That is, the deformation occurs in a direction of increasing a volume of the medium chamber. In contrast, when the P2 is lower than the P1, the hollow film 58g is expanded and deformed. That is, the deformation occurs in a direction of reducing the volume of the medium chamber. When the hollow film 58 is deformed, the two flat longitudinal side surfaces 72a, 72b each having a relatively large area are deformed. In other words, since any one of the two lateral side surfaces and the tip end surface has a relatively small area and is rounded, they are not so deformed compared with the two longitudinal side surfaces 72. According to the configuration of the embodiment, in both shrunk deformation and expanded deformation of the two longitudinal side surfaces 72a, 72b, it is basically possible to suppress an increase in the protrusion amount of the diaphragm 54, and in general, the protrusion amount of the diaphragm 54 is considered to be decreased. When the protrusion amount of the hollow film 58 is greatly expanded toward the living body side during deformation, a problem of being in contact with the transducer unit 22 may occur, but if the two longitudinal side surfaces 72a, 72b are deformed dominantly, such a problem can be avoided. Of course, depending on an internal structure of the ultrasonic probe, other forms may be adopted as a form of the hollow film 58 or the diaphragm 54.

The hollow film 58 is made of a rubber material, so that ultrasonic absorption affected by the hollow film 58 can be expected. In general, multiple reflection of the ultrasonic wave occurs in the ultrasonic probe, which causes deterioration in image quality. If such unnecessary ultrasonic wave reaches the hollow film 58, the ultrasonic wave is absorbed (see reference numerals 86, 88). In the embodiment, since two hollow films exist on both sides of the transducer unit, and since each hollow film has a flat and large longitudinal side surface facing a side of the transducer unit, unnecessary ultrasonic waves are effectively suppressed.

Since a tip end portion 58A of the hollow film 58 has a dome shape when viewed from the longitudinal direction, it is possible to expect that the turbulent flow that may occur when the acoustic propagation medium collides with the hollow film 58 is reduced. In addition, such a dome shape can prevent the cable from being caught when the cable is in contact with the tip end portion 58A.

As described above, when there is the empty space in the medium chamber, if the diaphragm is provided therein, the filling amount of the acoustic propagation medium can be reduced, and the weight of the ultrasonic probe can be reduced accordingly. In the above embodiment, two diaphragms are provided, but three or more diaphragms may be provided. Even when one diaphragm is provided, an advantage such as a reduction in the amount of acoustic propagation medium is obtained, but if two diaphragms are provided symmetrically when viewed from a center in the medium chamber, the weight balance can be improved.

The invention claimed is:

1. An ultrasonic probe comprising:
   a case comprising a film body, the film body comprising an outer surface configured to contact a surface of a living body that is an object of an ultrasonic diagnosis;
   a partition wall that is disposed in the case;
   a scanning mechanism configured to mechanically swing a transducer unit transmitting and receiving ultrasonic waves, along a mechanical scanning direction in a medium chamber that is formed between an inner surface of the film body and an inner surface of the partition wall, the inner surface of the partition wall facing the inner surface of the film body; and
   a pair of diaphragms, one provided on each side of the transducer unit in the mechanical scanning direction in the medium chamber, that has a form protruding in a direction from the inner surface of the partition wall towards the inner surface of the film body and the surface of the living body that is the object of the ultrasonic diagnosis, and that is configured to adjust internal pressure of the medium chamber, inside of each of the pair of diaphragms being filled with air.

2. The ultrasonic probe according to claim 1, wherein an atmospheric pressure chamber is formed between the case and an outer surface of the partition wall, and an inside of each of the diaphragms communicates with the atmospheric pressure chamber.

3. The ultrasonic probe according to claim 1, wherein the pair of the diaphragms are provided on both sides of the transducer unit in the mechanical scanning direction, so that a condition that the pair of the diaphragms does not come into contact with the transducer unit is satisfied even when the transducer unit to be mechanically scanned is the closest to the pair of the diaphragms.

4. The ultrasonic probe according to claim 1, wherein the scanning mechanism swings the transducer unit around a rotation central axis orthogonal to a probe central axis, and each of the diaphragms is a hollow member including a pair of longitudinal side surfaces extending in a longitudinal direction parallel to the rotation central axis and a pair of lateral side surfaces provided between the two longitudinal side surfaces.

5. The ultrasonic probe according to claim 4, wherein an end portion of a living body side in each of the diaphragms has a rounded dome shape when viewed from the longitudinal direction.

6. The ultrasonic probe according to claim 1, wherein each of the diaphragms includes:
   a pedestal attached to the partition wall; and
   a hollow film attached to the pedestal and elastically deformed, and
   a vent passage that communicates with an inside of the diaphragm and a space outside the partition wall is formed for each of the diaphragms.

7. The ultrasonic probe according to claim 6, wherein an attachment structure is provided across the diaphragm and the partition wall for each of the diaphragms, each attachment structure includes:
   a protruding portion formed on one of the pedestal and the partition wall; and
   a hole portion formed in another of the pedestal and the partition wall, and into which the protruding portion is inserted, and
   the vent passage is formed so as to penetrate each attachment structure.

8. The ultrasonic probe according to claim 7, wherein the protruding portion is formed on the pedestal, a through hole is formed along a central axis of the protruding portion, and the hole portion is an attaching hole which is formed in the partition wall and into which the protruding portion is inserted.

9. The ultrasonic probe according to claim 6, wherein in each of the diaphragms, the hollow film includes an attachment end portion that covers a side peripheral surface of the pedestal, and each of the diaphragms includes a band that suppresses the attachment end portion from an outside of the attachment end portion to the side peripheral surface of the pedestal.

* * * * *